United States Patent
Kim et al.

(10) Patent No.: US 9,290,743 B2
(45) Date of Patent: Mar. 22, 2016

(54) L-ASPARTATE OXIDASE VARIANT AND A METHOD FOR PRODUCING QUINOLINATE OR NICOTINIC ACID USING THE SAME

(71) Applicant: CJ CHEILJEDANG CORP., Seoul (KR)

(72) Inventors: So Young Kim, Gwacheon-si (KR); Yong Uk Shin, Yongin-si (KR); In Kyung Heo, Seoul (KR); Ju Eun Kim, Seoul (KR); Kwang Ho Na, Seoul (KR); Chang Il Seo, Incheon (KR); Sung Kwang Son, Seoul (KR); Jae Hee Lee, Seoul (KR)

(73) Assignee: CJ CHEILJEDANG CORP. (KR)

( * ) Notice: Subject to any disclaimer, the term of this patent is extended or adjusted under 35 U.S.C. 154(b) by 0 days.

(21) Appl. No.: 14/341,137

(22) Filed: Jul. 25, 2014

(65) Prior Publication Data
US 2015/0031093 A1     Jan. 29, 2015

(30) Foreign Application Priority Data
Jul. 25, 2013  (KR) .......................... 10-2013-0088240

(51) Int. Cl.
*C12N 9/06*   (2006.01)
*C12P 17/12*  (2006.01)

(52) U.S. Cl.
CPC ............... *C12N 9/0022* (2013.01); *C12P 17/12* (2013.01); *C12Y 104/03016* (2013.01)

(58) Field of Classification Search
IPC ........................................................ C12P 17/12
See application file for complete search history.

(56) References Cited

FOREIGN PATENT DOCUMENTS

| CN | 101353322 | 1/2009 |
| KR | 1020060068505 | 6/2006 |
| KR | 1020120082673 | 7/2012 |
| WO | 2012/096553 | 7/2012 |
| WO | 2013/103246 | 7/2013 |

OTHER PUBLICATIONS

Nasu, et. al.,"L-Aspartate Oxidase, a Newly Discovered Enzyme of *Escherichia coli*, Is the B Protein of Quinolinate Synthetase", The Journal of Biological Chemistry, vol. 257, No. 2, p. 626-632, Jan. 25, 1982.
Gerhardt, P., et al., •Manual of Methods for General Bacteriology, American Society for Bacteriology, p. 1-5, 1981.
Lee, James M., Biochemical Engineering, Prentice Hal International Editions, Chapter 6 Cell Kinetics and Fermenter Design, p. 138-176, 2009.
Hayashi, K., et al., "Highly Accurate Genome Sequences of *Escherichia coli* K-12 Strains MG1655 and W3110", Molecular Systems Biology, p. 1-5, 2006; vol. 2: 2006.0007, Epub Feb. 21, 2006.
Hughes, K.T., et al.,"6-Aminonicotinamide-Resistant Mutants of Salmonella Typhimurium", Journal of Bacteriology, vol. 154, No. 3, p. 1126-1136, Jun. 1983.
European Search Report dated Dec. 3, 2014 in European Patent Application No. 14178598.0, which corresponds to U.S. Appl. No. 14/341,137.
Ahmed Belmouden, et al., "Molecular cloning and nucleotide sequence of cDNA encoding rat kidney long-chain L-2-hydroxy acid oxidase Expression of the catalytically active recombinant protein as a chimaera", Eur. J. Biochem. 214, 17-25, 1993.
K. H. Diep Le, et al., "Amino Acid Sequence of Long Chain Hydroxy Acid Oxidase from Rat Kidney, a Member of the Family of FMN-dependent Hydroxy Acid-oxidizing Enzymes", vol. 266, No. 31, Issue of Novembner 5, pp. 20877-20881, 1991.
Michele Mortarino, et al., "L-Aspartate oxidase from Excherichia coli I. Characterization of coenzyme binding and product inhibition", Eur. J. Biochem. 239, 418-426, 1996.
Jochen Seipert, et al., "Expression of the *E coli* nadB Gene and Characteruzation of the Gene Product L-Aspartate Oxidase", Biol. Chem. Hoppe-Seyler, vol. 371, pp. 239-248, Mar. 1990.

*Primary Examiner* — Suzanne M Noakes
(74) *Attorney, Agent, or Firm* — Cantor Colburn LLP

(57) ABSTRACT

To produce quinolinate effectively, a L-aspartate oxidase variant that the feedback regulation by nicotinic acid or NAD is released, and a microorganism including the L-aspartate oxidase variant are provided. Quinolinate may be effectively produced by culturing of the microorganism including the L-aspartate oxidase variant.

11 Claims, 1 Drawing Sheet

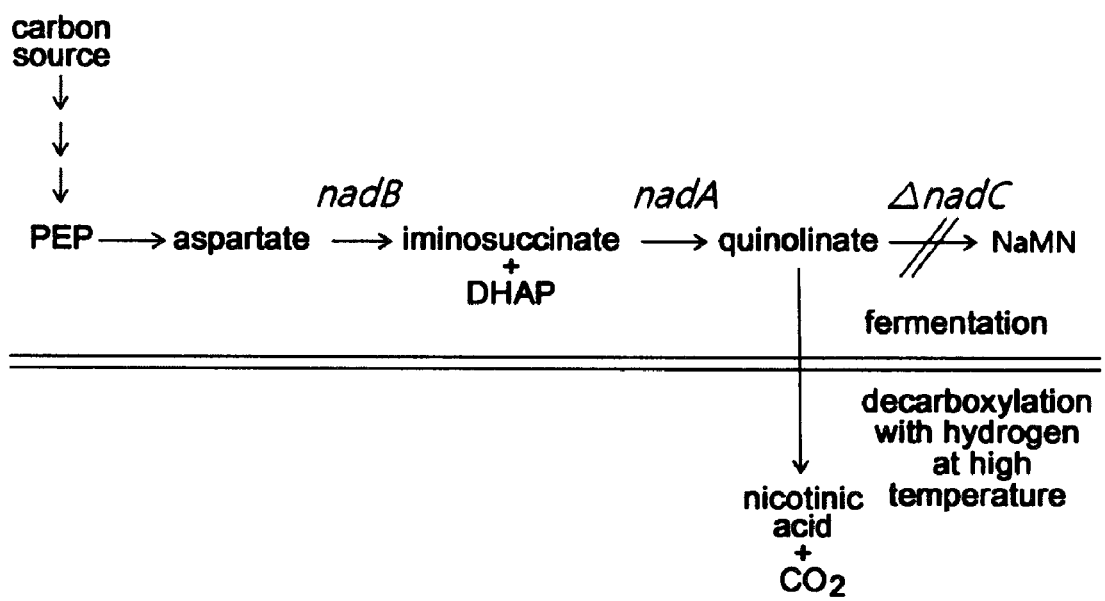

L-ASPARTATE OXIDASE VARIANT AND A METHOD FOR PRODUCING QUINOLINATE OR NICOTINIC ACID USING THE SAME

TECHNICAL FIELD

The invention relates to L-aspartate oxidase variants, quinolinate-producing microorganisms including genes that encode the L-aspartate oxidase variants, and methods of producing quinolinate or nicotinic acid in high efficiency by using the microorganisms.

BACKGROUND ART

Nicotinic acid is an oxide of nicotine and one of vitamin B complex. It is a water soluble vitamin, which is also called niacin, or vitamin $B_3$ and prevalent in animal and plant. Deficiency of nicotinic acid may cause pellagra disease or neuropathies. In general, nicotinic acid is present in the form of nicotinic acid amide coenzyme, i.e., nicotinamide adenine dinucleotide (NAD) or nicotinamide adenine dinucleotide phosphate (NADP), in vivo, and is involved in oxidation reduction reactions.

Quinolinate, which is also called quinolinic acid, is produced by oxidation of quinoline. Quinolinic acid is known to have neurotoxicity and cause various neurological disorders. Quinolinate is also known as a precursor of nicotinic acid.

Nicotinic acid that is widely applicable to the foods and medicinal products may be prepared by a chemical synthetic method or a biological production method. Chemical synthesis of nicotinic acid may result in large quantities of toxic waste including catalysts. Thus, the waste is required for a thorough management and great expenses for disposal. In addition, pyrimidine used as a precursor has various derivatives, and then fluctuations in supply and price of pyrimidine cause an unstable price of nicotinic acid.

To solve the such problems from the chemical synthesis method, biological methods of producing nicotinic acid by using renewable carbohydrate-derived materials have been studied. Biological production of nicotinic acid is accomplished mainly through two biosynthetic pathways, one of which is a biosynthetic pathway of nicotinic acid from tryptophan as a starting material in eukaryotes, and the other is from aspartic acid as a starting material as in prokaryotes. Both of the pathways use quinolinate as an intermediate, and biosynthesize nicotinic acid from quinolinate by the action of quinolinate phosphoribosyltransferase (nadC), nicotinate-mononucleotide adenyl transferase (nadD), NAD synthetase (nadE), nicotinamide-nucleotide adenyl transferase (NMN nadR), and nicotinamidase (pncA).

Biological synthesis methods of nicotinic acid by using recombinant *E. coli* or *Corynebacterium glutamicum* via the pathway of aspartic acid is disclosed (Korean Patent No. 10-1223904). While the inventors of the present invention researched to address the problems from such biological synthesis methods of nicotinic acid and to improve the yield of quinolinate or nicotinic acid, they found enzyme variants involved in the high-yield production of quinolinate and completed the present invention.

DETAILED DESCRIPTION OF THE INVENTION

Technical Problem

The invention provides L-aspartate oxidase variants showing that the feedback regulation by nicotinic acid or nicotinamide adenine dinucleotide (NAD) is released.

The invention provides quinolinate-producing microorganisms that include the L-aspartate oxidase variants.

The invention provides methods of producing quinolinate by culturing the microorganisms.

The invention provides methods of producing nicotinic acid by culturing the microorganisms and decarboxylation of quinolinate.

Technical Solution

An aspect of the present invention provides an L-aspartate oxidase variant having an amino acid sequence which a $302^{nd}$ amino acid in amino acid sequence represented by SEQ ID NO: 1 is substituted with another amino acid.

L-aspartate oxidase has a catalytic activity of oxidizing L-aspartate to iminosuccinate, as represented in Reaction Scheme 1.

<Reaction Scheme 1>

L-Aspartate+Fumarate$\Longleftrightarrow$α-iminosuccinate+Succinate+H

L-Aspartate+Oxygen$\Longleftrightarrow$Hydrogen peroxide+α-iminosuccinate+$H^+$

L-aspartate oxidase of the present invention may comprise the amino acid sequence represented by SEQ ID NO: 1. However, it is not limited thereto, because there may be the difference in the amino acid sequence of the protein depending on the microbial species or strains. In other words, it can be a mutant protein or artificial variant with an amino acid sequence comprising substitution, deletion, insertion, or addition of one or several amino acids at one or more locations of the amino acid sequence of represented by SEQ ID NO: 1, as long as it can oxidize L-aspartate to iminosuccinate. Herein, "several" may differ depending on the location or type in the three-dimensional structure of amino acid residues of the protein, but specifically means 2 to 20, specifically 2 to 10, and more specifically 2 to 5. In addition, the substitution, deletion, insertion, addition or inversion of the amino acid includes those caused by artificial variants or natural mutation, if based on the difference in the individual or species of microorganism.

The polynucleotide encoding the amino acid sequence in of the present invention may comprise the polynucleotide sequence encoding the protein having amino acid sequence represented by SEQ ID NO: 1, or the amino acid sequence of 80% or more, specifically 90% or more, more specifically 95% or more, and particularly specifically 97% or more homology with the same, as long as it has similar activity as L-aspartate oxidase. The most specifically, it may be the polynucleotide sequence represented by SEQ ID NO: 24.

The term "homology" refers to the identity between two amino acid sequences and canmay be determined by the well known method well known to those skilled in the art, using BLAST 2.0 to compute the parameter such as score, identity and similarity.

In addition, the polynucleotide sequence encoding L-aspartate oxidase of the present invention can be hybridized with the polynucleotide of SEQ ID. NO: 24 or the probe prepared from the same under 'stringent conditions', and can may be a variant modified polynucleotide sequence encoding L-aspartate oxidase which normally functions. As used herein, "stringent conditions" refer to conditions which allow the specific hybridization between the polynucleotide, and are described specifically, for example, in Molecular Cloning (A Laboratory Manual, J. Sambrook et al., Editors, 2nd Edition, Cold Spring Harbor Laboratory press, Cold Spring Harbor, N.Y., 1989) or Current Protocols in Molecular Biology (F. M. Ausubel et al., Editors, John Wiley & Sons, Inc., New York). For example, which describes, for example, the hybridization is carried out in the hybridization buffer of 65° C. (3.5×SSC, 0.02% Ficoll, 0.02% polyvinylpyrrolidone, 0.02% bovine serum albumin, 2.5 mM NaH2PO4 (pH 7), 0.5% SDS, 2 mM EDTA). SSC is 0.15 M sodium chloride/ 0.15 M sodium citrate of pH 7. After hybridization, the membrane to which DNA is delivered transferred to is rinsed with 2×SSC at room temperature and then cleansed rinsed again with 0.1 to 0.5×SSC/0.1×SDS at a temperature of 68° C.

As used herein, the term "an another amino acid" refers to the other amino acid residue except the amino acid originally located in the amino acid sequence prior to the modification. Specifically the another amino acid of the present invention may include one amino acid selected from the group consisting of arginine, glycine, alanine, serine, threonine, cysteine, valine, leucine, isoleucine, methionine, proline, phenylalanine, tyrosine, tryptophan, aspartic acid, glutamic acid, asparagine, glutamine, and histidine except lysine. Specifically, the another amino acid may include one amino acid selected from the group consisting of arginine, valine, leucine, isoleucine, methionine, tryptophan, and histidine. For example, the another amino acid may include arginine.

As used herein, the term "$302^{nd}$" refers to the position of amino acid from the methionine of the amino acid sequence represented by SEQ ID NO: 1, since the methionine of the amino acid sequence is counted to the first amino acid residue.

In general, the activity of L-aspartate oxidase is regulated by nicotinic acid or NAD accumulated in microorganisms, in other words, its feedback regulation is inhibited by nicotinic acid or NAD. The feedback regulation by nicotinic acid of NAD may be released in the L-aspartate oxidase variants of the present invention, unlike common L-aspartate oxidase.

The other aspect of the present invention provides a polynucleotide having a nucleotide sequence that encodes for the L-aspartate oxidase variants.

In an embodiment of the present invention, a polynucleotide may have a nucleotide sequence that encodes a L-aspartate oxidase variant having an amino acid sequence which a $302^{nd}$ amino acid in the amino acid sequence represented by SEQ ID NO:1 is substituted with another amino acid.

The $302^{nd}$ amino acid may include one amino acid selected from the group consisting of arginine, glycine, alanine, serine, threonine, cysteine, valine, leucine, isoleucine, methionine, proline, phenylalanine, tyrosine, tryptophan, aspartic acid, glutamic acid, asparagine, glutamine, and histidine. Accordingly, the nucleotide sequence corresponding to the $302^{nd}$ amino acid may be appropriately substituted. In a specific embodiments, $904^{th}$ to $906^{th}$ nucleotides in a nucleotide sequence represented by SEQ ID NO:24 may be appropriately substituted with any combination of nucleotides except for AAG, AAA, TAA, TAG, and TGA.

Another aspect of the present invention, provides a vector including an above-described polynucleotide, which is operably linked to a regulatory sequence.

The polynucleotide may have a nucleotide sequence that $904^{th}$ to $906^{th}$ nucleotides in the nucleotide sequence represented by SEQ ID NO: 24 are appropriately substituted. In a specific embodiment, the polynucleotide may have a nucleotide sequence that $904^{th}$ to $906^{th}$ nucleotides in the nucleotide sequence represented by SEQ ID NO: 24 are substituted with any combination of nucleotides except for AAG, AAA, TAA, TAG, and TGA. The polynucleotide may be operably linked to a regulatory sequence. The regulatory sequence may regulate expression of L-aspartate oxidase, and include a promoter, a terminator, or an enhancer.

The vector of the present invention is not specifically limited, and may be any vector known in the art. For example, the vector may be pCR2.1-TOPO vector (Invitrogen, U.S.A) or pECCG117 (KFCC-10673), but it's not limited thereof.

The promoter of the present invention may be a lambda PL promoter, a trp promoter, a lac promoter, a T7 promoter, a pPro promoter, a pCJ1 promoter, or a pCJ7 promoter (Korean Patent No. 10-0620092). In a specific embodiment, the promoter may be a pCJ1 promoter, but it's not limited thereof.

The promoter may be operably linked to a nucleotide sequence encoding a gene. As used herein, the term "operably linked" refers to a functional linkage between a nucleic acid expression regulatory sequence (for example, a: promoter, a signal sequence, an array of transcriptional regulatory factor binding sites, a terminator, or an enhancer) and other nucleotide sequences. Accordingly, the regulatory sequence may regulate transcription and/or translation of the nucleotide sequence encoding the gene.

Another aspect of the present invention provides a microorganism comprising an above-described polynucleotide, wherein the polynucleotide may comprise a nucleotide sequence enencoding an amino acid sequence which $302^{nd}$ amino acid in the amino acid sequence represented by SEQ ID NO: 1 is substituted with another amino acid.

In a specific embodiments, according to the substitution of the $302^{nd}$ amino acid in the amino acid sequence of SEQ ID NO: 1, part of a nucleotide sequence of SEQ ID NO: 24 may be substituted. For example, the polynucleotide may comprise a polynucleotide that $904^{th}$ to $906^{th}$ nucleotides in the nucleotide sequence of SEQ ID NO: 24 are substituted with other nucleotides.

The polynucleotide may be obtained through random mutation or genetic engineering manipulation. A microorganism, in which part of an amino acid sequence of SEQ ID NO: 1 is partially substituted, may be constructed by transformation of the obtained polynucleotide.

As used herein, the term "transformation" refers to introducing a gene into a host cell to be expressed therein. The transformed gene may be in any gene, for example, that is inserted into a chromosome of the host cell, or that is out of the chromosome of the host cell, as long as the introduced gene is expressible within the host cell. The gene includes a polynucleotide encoding a polypeptide, such as DNA and RNA. For example, the gene may be introduced in the form of an expression cassette, which is a polynucleotide structure including all the elements required for self-expression of the gene, into a host cell. Typically, the expression cassette may include a promoter operably linked to the gene, a transcription termination signal, a ribosome binding site, and a translation termination signal. The expression cassette may be in the form of an expression vector that is self-replicable. The gene may also be introduced into a host cell by itself or in the form of a polynucleotide structure and operably linked to a sequence that is required for expression in the host cell.

As used herein, the term "microorganism having an ability to produce quinolinate" refers to a microorganism capable of producing quinolinate from a carbon source in a culture medium and of accumulating quinolinate.

To improve the ability to produce quinolinate, it is required that microorganisms produce large quantities of quinolinate, and the produced quinolinate can be accumulated without being used in other ways. Therefore, in some embodiments of the present invention, the microorganism having an improved ability to produce quinolinate may be obtained by removing or weakening the activity of quinolinate phosphoribosyltransferase that is involved in a decomposition pathway of quinolinate, by enhancing the expression or activity of quinolinate synthetase that is involved in a synthetic pathway of quinolinate, or by a combination thereof.

In a specific embodiment, the microorganism having an improved ability to produce quinolinate may be further modified to enhance the activity of quinolinate synthetase. Specifically, the enhanced activity of the quinolinate synthetase may be achieved by additionally introducing the quinolinate synthetase to increase the expression thereof in the microorganism. The enhanced activity of the quinolinate synthetase may also be achieved by replacing a promoter linked to the quinolinate synthetase in the microorganism with a strong promoter. In addition, the enhanced activity of the quinolinate synthetase may be achieved by increasing the activity of the quinolinate synthetase itself.

In the case where the heterogenous quinolinate synthetase is introduced, a polynucleotide encoding this enzyme may be introduced to increase the expression of the polynucleotide. The polynucleotide encoding the quinolinate synthetase may be expressed in a plasmid of the microorganism or may be inserted into a chromosome of the microorganism and expressed therein.

The quinolinate synthetase may have an amino acid sequence represented by SEQ ID NO: 29 or may have an amino acid sequence that is homologous thereto. In other words, it is not limited thereto, because there may be the difference in the amino acid sequence of the protein depending on the microbial species or strains. It can be a mutant protein or artificial variant with an amino acid sequence comprising substitution, deletion, insertion, or addition of one or several amino acids at one or more locations of the amino acid sequence of represented by SEQ ID NO: 29, as long as it can synthesize quinolinic acid from iminosuccinic acid. The sequence of gene nadA enencoding this enzyme can be obtained from the genome sequence (gi: GI:89109380) of *Escherichia coli* (*E. coli*) as disclosed in an article (Mol Syst Biol., 2006; 2:2006.0007, Epub 2006 Feb. 21) or the database available from the National Center for Biotechnology Information (NCBI) or the DNA Data Bank of Japan (DDBJ). Also, the polynucleotide encoding the amino acid sequence in of the present invention may comprise the polynucleotide sequence encoding the protein having amino acid sequence represented by SEQ ID NO: 29, or the amino acid sequence of 80% or more, specifically 90% or more, more specifically 95% or more, and particularly specifically 97% or more homology with the same, as long as it has similar activity as L-aspartate oxidase. The most specifically, it may be the polynucleotide sequence represented by SEQ ID NO: 26.

The quinolinate synthetase has an activity to synthesize quinolinic acid from iminosuccinic acid, as shown in Reaction Scheme 2.

<Reaction Scheme 2>
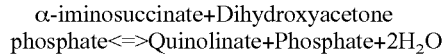
α-iminosuccinate+Dihydroxyacetone phosphate<=>Quinolinate+Phosphate+2H$_2$O Therefore, when the expression of a gene encoding the quinolinate synthetase or the activity of this enzyme is enhanced, the yield of quinolinate in cells may be increased.

In some embodiments, in the microorganism having an ability to produce quinolinate, the activities of aspartic acid oxidase and quinolinate synthetase may be enhanced by substituting endogenous promoters with strong promoters, by inducing a mutation in the promoters, or by increasing the copy number of the genes. For the substitution with strong promoters, generally known strong promoters, including pTac, pTrc, pPro, pR, pL, pCJ1, pCysK, and the like, may be used.

In a specific embodiment, there is provided a microorganism having an improved ability to produce quinolinate, wherein the activity of quinolinate phosphoribosyltransferase may be additionally reduced or removed.

The activity of quinolinate phosphoribosyltransferase may be reduced or removed by modifying a gene encoding quinolinate phosphoribosyltransferase or by using a microRNA that suppresses transcription.

The quinolinate phosphoribosyltransferase may have an amino acid sequence represented by SEQ ID NO: 30 or an amino acid sequence that is highly homologous thereto. In other words, it is not limited thereto, because there may be the difference in the amino acid sequence of the protein depending on the microbial species or strains. It can be a mutant protein or artificial variant with an amino acid sequence comprising substitution, deletion, insertion, or addition of one or several amino acids at one or more locations of the amino acid sequence of represented by SEQ ID NO: 30, as long as it can synthesize nicotinic acid (nicotinate) mononucleotide from quinolinate.

The quinolinate phosphoribosyltransferase may have an activity to synthesize nicotinic acid mononucleotide from quinolinate, as shown in Reaction Scheme 3. Therefore, the yield of quinolinate in cells may be increased by deleting a gene having the activity to synthesize nicotinic acid mononucleotide or by weakening the activity of the gene.

<Reaction Scheme 3>
5-Phospho-α-D-ribose 1-diphosphate+Quinolinate+2H$^+$ <=>CO$_2$+Diphosphate+Nicotinate ribonucleotide
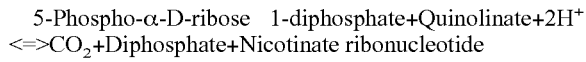

Weakening or removing the activity of quinolinate phosphoribosyltransferase may be performed by substituting an endogenous gene encoding quinolinate phosphoribosyltransferase with a modified gene to weaken or remove the activity of the enzyme, by replacing a promoter of the endogenous gene with a weak promoter, or by deleting the endogenous gene encoding the enzyme from chromosome.

In a specific embodiment, in the microorganism having an improved activity to produce quinolinate, the activity of quinolinate phosphoribosyltransferase converting quinolinate into nicotinic acid mononucleotide may be removed. To this end, the gene nadC encoding quinolinate phosphoribosyltransferase may be removed from the genome of the microorganism by homologous recombination. The sequence of the gene nadC may be obtained from the genome sequence (GI:89106990) of *E. coli* as disclosed in an article (Mol Syst Biol., 2006; 2:2006.0007, Epub 2006 Feb. 21), or the database available from the National Center for Biotechnology Information (NCBI) or the DNA Data Bank of Japan (DDBJ). Also, the polynucleotide encoding the amino acid sequence in of the present invention may comprise the polynucleotide sequence encoding the protein having amino acid sequence represented by SEQ ID NO: 30, or the amino acid sequence of 80% or more, specifically 90% or more, more specifically 95% or more, and particularly specifically 97% or more homology with the same, as long as it has similar activity as L-aspartate oxidase. The most specifically, it may be the polynucleotide sequence represented by SEQ ID NO: 25.

In a specific embodiment, the microorganism having an ability to produce quinolinate may be a prokaryotic microorganism or an eukaryotic microorganism.

In some embodiments, examples of the microorganism having an ability to produce quinolinate may belong to the genus *Enterbacter*, genus *Escherichia*, genus *Erwinia*, genus *Serratia*, genus *Providencia* genus, genus *Corynebacterium*, and genus *Brevibacterium*, but it's not limited thereto.

In a specific embodiment, the microorganism having an ability to produce quinolinate may be belong to the genus *Escherichia*.

Specifically, the microorganism having an ability to produce quinolinate may be *Escherichia coli* (*E. coli*).

Another aspect of the present invention provides a method of producing quinolinate, comprising: culturing a microorganism that includes a polynucleotide encoding a L-aspartate oxidase which a $302^{nd}$ amino acid in an amino acid sequence represented by SEQ ID NO:1 is substituted with another amino acid; and recovering quinolinate from a cultured solution.

The culturing of the microorganism may be performed using a suitable culture medium under suitable culture conditions that are well-known in the art. Such culturing procedures may be used by one of ordinary skill in the art and may be readily adjusted depending on a selected microorganism. The culturing method may include a batch culture type, a continuous culture type, and a fed-batch culture type, but it's not limited thereto. Various examples of culturing methods are disclosed in, for example, "Biochemical Engineering" (by James M. Lee, Prentice-Hall International Editions, pp 138-176").

The culture medium used in the culturing process is required to satisfy suitable conditions for a selected microorganism. Various culture media for microorganisms are disclosed in, for example, "Manual of Methods for General Bacteriology (by the American Society for Bacteriology, Washington D.C., U.S.A, 1981)". For example, the culture medium may include various carbon sources, nitrogen sources, and trace elements.

Examples of carbon sources available for the culture medium may include carbohydrates, such as glucose, sucrose, lactose, fructose, maltose, and starch; oils and fats, such as soybean oil, sunflower oil, castor oil, and coconut oil; fatty acids, such as palmitic acid, stearic acid, and linoleic acid; alcohols, such as glycol and ethanol; and organic acids, such as acetic acid, which may be used alone or in combination, but it's not limited thereto Examples of nitrogen sources available for the culture medium may include organic nitrogen sources, such as peptones, yeast extract, meat extract, malt extract, corn steep liquor (CSL), soybean flour, and urea; and inorganic nitrogen sources, such as ammonium sulfate, ammonium chloride, ammonium phosphate, ammonium carbonate, and ammonium nitrate, which may be used alone or in combination, but it's not limited thereto.

Examples of phosphorous sources available for the culture media may include potassium dihydrogen phosphate, dipotassium hydrogen phosphate, and corresponding sodium-containing salts. In some embodiments, the culture medium may also include metal salts such as magnesium sulfate or iron sulfate. In some embodiments, the culture medium may further include amino acids, vitamins, and suitable precursors, in addition to the above-listed components. The culture medium for culturing microorganisms, or individual components may be added to a culture solution in a batch or continuous manner.

In some embodiments, during the culture, the pH of the culture solution may be adjusted by adding a compound, for example, ammonium hydroxide, potassium hydroxide, ammonia, phosphoric acid, or sulfuric acid in a proper manner. In addition, during the culture, foaming in the culture solution may be suppressed using an anti-foaming agent such as a fatty acid, for example, polyglycol ester. To keep the culture solution in an aerobic condition, oxygen or an oxygen-containing gas (for example, air) may be supplied into the culture solution. The temperature of the culture solution may be maintained in a temperature range of about 20☐ to about 45☐, specifically about 25☐ to about 40☐. The culturing may be maintained until a target quantity of quinolinate is obtained, specifically, the period may be about 10 hours to 160 hours.

Another aspect of the present invention provides a method of producing nicotinic acid, comprising: culturing a microorganism that includes a polynucleotide encoding L-aspartate oxidase which $302^{nd}$ amino acid in an amino acid sequence represented by SEQ ID NO:1 is substituted with another amino acid; and conducting decarboxylation reaction by adding an acid to a cultured product.

As used herein, the term "decarboxylation reaction" refers to a reaction to produce nicotinic acid by removing a carboxyl group from quinolinate and releasing carbon dioxide.

In particular, after the culturing of the microorganism, the resulting quinolinate-including culture solution may be subjected to centrifugation or membrane filtration to remove the microorganism. Then, to accelerate the decarboxylation reaction, an acid that provides a hydrogen group may be added into the quinolinate-including culture solution. Any acid may be used without limitation, as long as it can provide hydrogen group to the culture solution.

In an embodiment, the quinolinate-including culture solution may be used without purification.

In an embodiment, the acid being added into the culture solution may be hydrochloric acid or sulfuric acid.

In an embodiment, after the addition of the acid, the culture solution may be have a pH of about 5 or less, or may specifically be in a range of about 2 to about 3.

In an embodiment, the decarboxylation reaction of the culture solution may be performed at a temperature of about 100☐ to about 150☐, or may specifically be in a range of about 120☐ to about 135☐.

In an embodiment, the decarboxylation reaction of the culture solution may be performed at a pressure of about 0.1 MPa to about 0.5 Mpa, or may specifically be performed at a pressure of about 0.2 MPa to about 0.4 MPa.

Upon conducting the decarboxylation under high-temperature and high-pressure conditions for about 1 hour to 3 hours after the addition of an acid into the quinolinate-including culture solution, quinolinate in the culture solution may be converted into nicotinic acid, as shown in Reaction Scheme 4.

<Reaction Scheme 4>

Quinolinate+2H+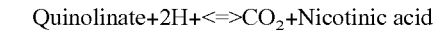$CO_2$+Nicotinic acid

In an embodiment, the method of producing nicotinic acid may further include recovering and purifying the nicotinic acid.

In an embodiment, the recovering of nicotinic acid may be conducted by a common method known in the art, including filtration of the culture solution and crystallization processes.

Advantageous Effects

According to embodiments of the present invention, quinolinate may be effectively produced by culturing a microorganism including a L-aspartate oxidase variant that the feedback regulation by nicotinic acid or NAD. Nicotinic acid is released. These methods using the microorganism may solve the problems from the conventional chemical synthesis methods, regarding environmental issues due to generation of catalyst byproducts, high-energy consumption and use of non-renewable resources, and the problem of low yield with the conventional biosynthesis methods. Consequently, these methods may efficiently produce quinolinate and nicotinic acid in an environmental-friendly manner.

DESCRIPTION OF THE DRAWINGS

FIG. 1 illustrates a pathway to produce nicotinic acid in a method of producing nicotinic acid according to an embodiment of the present invention.

MODE OF THE INVENTION

The present invention will be described in further detail with reference to the following examples. These examples are for illustrative purposes only and are not intended to limit the scope of the invention.

Example 1

Preparation of L-Aspartate Oxidase Variants NAD-Feedback Regulation is Released

<1-1> Construction of Plasmid Expressing L-Aspartate Oxidase

To prepare L-aspartate oxidase variants, an *E. coli*-derived nadB gene encoding the wild L-aspartate oxidase was cloned in an expression vector. To this end, a chromosome of *E. coli* K12 W3110 strain was used as a template. The strain was purchased from the American Type Culture Collection (ATCC No. 23257). Based on the nucleotide sequence for the nadB gene (NCBI Registration No. "GI:89109380") represented by SEQ ID NO: 24 obtained from the GenBank of the National Institute of Health (NIH GenBank). Primers of SEQ ID NOs: 2 and 3 having the recognition sites of restriction enzymes NdeI and BamHI are constructed to amplify the ORF region of the nadB gene, for gene cloning.

TABLE 1

| Nucleotide sequence | SEQ ID NO |
|---|---|
| 5' AATTCATATGAATACTCTCCCTGAACATT 3' | 2 |
| 5' AATTGGATCCCTATACCACTACGCTTGATCAC 3' | 3 |

PCR was conducted using chromosomal DNA of *E. coli* K12 W3110 as the template and oligonucleotides represented by SEQ ID NOs: 2 and 3 as primers. The polymerase used was PfuUltra™ DNA polymerase (Stratagene, U.S.A.), and PCR was conducted by repeating 30 times of a cycle comprising denaturation at 96□ for 30 seconds, annealing at 50□ for 30 seconds, and extension at 72□ for 2 minutes. Through the PCR, an amplified gene of about 1.9 kb including the nadB ORF gene and the recognition sites of restriction enzymes NdeI and BamHI was obtained.

The nadB gene obtained through the PCR was recovered by agarose gel elution, and then treated with the restriction enzymes NdeI and BamHI, followed by ligation into a pPro-Lar vector (CloneTech, U.S.A) treated with the restriction enzymes NdeI and BamHI so as to express L-aspartate oxidase from the nadB gene linked to a pPro promoter. The resulting vector was named "pPro-nadB vector".

<1-2> Construction of Plasmid Library of L-Aspartate Oxidase Variant

To obtain L-aspartate oxidase variants, a nadB gene variant library was constructed using the pPro-nadB vector obtained in <1-1> as a template by error-prone PCR in the presence of dGTP and $MnSO_4$.

In the error-prone PCR using the pPro-nadB recombinant vector as a template, primers 4 and 5 were used, concentrations of dGTP and $MnSO_4$ in a PCR mix, which were used to control a GC rate and an error rate, were 2 mM and 8 mM, respectively, and the polymerase used was PfuUltra™ DNA polymerase (Stratagene, U.S.A.). PCR was conducted by repeating 30 times of a cycle comprising denaturation at 96□ for 30 seconds, annealing at 50□ for 30 seconds, and extension at 72□ for 2 minutes. Through the PCR, a DNA fragment of about 1.9 kb was obtained. This DNA fragment was purified via agarose gel elution, treated with the restriction enzyme DpnI (NEB, U.S.A) for about 1 hour, and then transformed into *E. coli* DH5α strain (Invitrogen, U.S.A.) via $CaCl_2$ method. The transformed *E. coli* DH5a strain was smeared on a Luria-Bertani (LB)-kanamycin(Km) (yeast extract 10 g/L, NaCl 5 g/L, tryptone 10 g/L, kanamycin 25 μg/L) plate medium, and cultured overnight at 37□ to obtain kanamycin-resistant colonies. Ten clones were randomly selected from them, followed by sequencing. As a result, the error rate of the nadB gene was estimated to be about 4.5 nucleotide/1 kb. The number of strains with a nadB gene variant obtained was about $3 \times 10^5$ or more.

TABLE 2

| Nucleotide sequence | SEQ ID NO |
|---|---|
| 5' CTCGAGCATAGCATTTTTATCC 3' | 4 |
| 5' CAGTGAGCGAGGAAGCGG 3' | 5 |

<1-3> Selection of L-Aspartate Oxidase Variants Showing Released NAD-Feed Back Regulation <1-3-1> Construction of L-Aspartate Oxidase-Deficient Strain The nadB gene negatively affects on the production of quinolinate under the feedback regulation by NAD (J Biol Chem. 1982 Jan 25; 257(2):626-32.). For this reason, it is important to discover a nadB gene the feedback regulation by NAD is released. To effectively selecting better naB gene variants, an endogenous nadB gene was removed from a strain. Based on the nucleotide sequence for the nadB gene (NCBI Registration No. "GI:89109380") represented by SEQ ID NO: 24 obtained from the GenBank of the National Institute of Health (NIH GenBank), primers of SEQ ID NOs: 6 and 7 able to amplify the downstream region of the nadB gene, primers of SEQ ID NOs: 8 and 9 able to amplify the upstream region of the nadB gene, and primers of SEQ ID NOs: 10 and 11 able to amplify loxpCm were constructed.

TABLE 3

| Nucleotide sequence | SEQ ID NO |
|---|---|
| 5' CATTATACGAACGGTACCCCAAAGCCTGGGTCAG CGCCGT 3' | 6 |
| 5' GGCGGATATTCAGCAGTGG 3' | 7 |
| 5' CCCAAACCAAATTTCCACG 3' | 8 |
| 5' CGGTAGGTACCGAGCTCGAATTTCTTTGTTTAAT TTACTA 3' | 9 |
| 5' TAGTAAATTAAACAAAGAAATTCGAGCTCGGTAC CTACCG 3' | 10 |
| 5' ACGGCGCTGACCCAGGCTTTGGGGTACCGTTCG TATAATG 3' | 11 |

PCR was performed using a chromosomal DNA of *E. coli* K12 W3110 (ATCC NO. 23257) as a template and oligonucleotides of SEQ ID NOs. 6 and 7 as primers to amplify the upstream and SEQ ID NOs. 8 and 9 as primers to amplify downstream regions of nadB gene of 0.4 kb and 0.4 kb, respectively. In addition, PCR was performed using the plasmid vector containing loxpCm, pLoxpCat2 vector, as a template and oligonucleotides of SEQ ID NOs. 10 and 11 as primers to amplify loxpCm gene having the sequence homologous to nadB gene on both ends of 1.0 kb. The polymerase used was PfuUltra™ DNA polymerase (Stratagene, U.S.A), and the PCR was conducted by repeating 30 times of a cycle comprising denaturation at 96☐ for 30 seconds, annealing at 53☐ for 30 seconds, and extension at 72☐ for 1 minute, followed by agarose gel elution to obtain a nadB-upstream fragment, a nadB-downstream fragment, and a loxpCm fragment. PCR was conducted using these obtained fragments as templates under the PCR conditions by repeating 10 times of the cycle comprising denaturation at 96☐ for 60 seconds, denaturation at 50☐ for 60 seconds, and extension at 72☐ for 1 minute, and 20 repetition of the cycle after addition of primers of SEQ ID NOs. 7 and 8. As a result, a nadB-deficient cassette containing the upstream region of nadB gene-loxpCm-downstream region of nadB gene of 1.8 kb was obtained.

E. coli K12 W3110 strain containing pKD46 as lambda red recombinase expression vector was transformed with the nadB-deficient cassette by electroporation, and then the strain was smeared on a LB plate medium (tryptone 10 g, yeast extract 5 g, NaCl 10 g, chloramphenical 15 µg/L, and agar 1.5%) containing chloramphenicol as a selective marker. Then cultured at 37☐ overnight to select microorganism strains exhibiting resistance against chloramphenical.

The selected strains were directly used as templates to perform PCR using primers of SEQ ID NOs. 7 and 8 under the same conditions. The gene sizes of the wild strain and the nadB-deficient strain were identified to be 2.4 kb and 0.8 kb, respectively on 1.0% agarose gel, thereby confirming the deletion of nadB gene in E. coli K12 W3110. The construction of the nadB-deficient strain, named W3110-ΔnadB, was completed.

<1-3-2> Selection of L-Aspartate Oxidase Variants

To find a nadB gene resistant to the feedback regulation by NAD, 6-aminopyridine-3-carboxylic acid (6-NA, purchased from Aldrich, U.S.A) as a nicotinic acid analogue, and 6-aminonicotinamide (6-Nm, purchased from Aldrich, U.S.A) as a nicotinamide analogue were used. Although a 6-NAD analogue should be used, due to the structural similarity of NAD with nicotinic acid and nicotinamide, resistant nadB gene variants were primarily selected using the nicotinic acid analogue and nicotinamide analogue, and then the NAD-feedback resistance of each of the selected nadB gene variants was confirmed (ref. Journal of bacteriology, June 1983, p. 1126-1136). L-aspartate oxidase variant plasmid library constructed in <1-2> of Example 1 was transformed into W3110-ΔnadB strain via $CaCl_2$ method.

The transformed W3110-ΔnadB strain was smeared on a M9-(6,NA)-(6,Nm) plate medium ($NaHPO_4$-$7H_2O$ 12.8 g, $KH_2PO_4$ 3 g, NaCl 0.5 g, $NH_4Cl$ 1 g, $MgSO_4$ 2 mM, $CaCl_2$ 0.1 mM, casamino acid 1 g, 6-aminopyridine-3-carboxylic acid (6-NA) 0.3 g/L, 6-aminonicotinamide (6-Nm) 0.3 g/L) to select colonies with higher growth rate compared to the wild nadB. A total of $1 \times 10^7$ colonies were screened and three of them were selected, and then named pPro-nadB64, pPro-nadB67, and pPro-nadB110, respectively. The selected three strains were each inoculated and cultured in a M9-(6,NA)-(6,Nm) liquid medium ($NaHPO_4$-$7H_2O$ 12.8 g, $KH_2PO_4$ 3 g, NaCl 0.5 g, $NH_4Cl$ 1 g, $MgSO_4$ 2 mM, $CaCl_2$ 0.1 mM, casamino acid 1 g, 6-aminopyridine-3-carboxylic acid (6-NA) 0.3 g/L, 6-aminonicotinamide (6-Nm) 0.3 g/L), and then optical densities (OD) thereof were compared. As a result, the growth rates of pPro-nadB67 were found to be higher than those of the pPro-nadB64 and pPro-nadB72 in the media containing 6-NA and 6-Nm, as shown in Table 4. Accordingly, the pPro-nadB67 was selected and sequence thereof was identified. As a result, the pPro-nadB67 was found to include arginine as substituent for lysine, the $302^{nd}$ amino acid from the start amino acid methione.

E. coli K12 W3110 which is deficient of nadC gene, and contains a pPro-nadB67(Lys302Arg)-pCJ-nadA by using pProlar vetor as an expression vector for nadB gene variant, was named CV01-0518. Then it was deposited under the Budapest Treaty at the Korean Culture Center of Microorganisms (KCCM) with Accession No. KCCM11434P on Jun. 20, 2013.

TABLE 4

Growth rate comparison of three nadB variants in a liquid media containing 6-NA and 6-Nm

| nadB name | OD (4 hr) | OD (12 hr) |
|---|---|---|
| pPro nadB | 0.24 | 1.06 |
| pPro nadB64 | 0.44 | 1.12 |
| pPro nadB67 | 0.62 | 1.30 |
| pPro nadB72 | 0.46 | 1.18 |

Example 2

Quinolinic Acid Yield Comparison Between nadB Gene Variants

<2-1> Construction of Quinolinate Phosphoribosyltransferase-Deficient Strain

PCR was conducted using on chromosomal DNA of E. coli K12 W3110 as a template to obtain a nadC gene that is involved in the decomposition pathway of quinolinate. Based on the nucleotide sequence for the nadC gene (NCBI Registration No. "GI:89106990") represented by SEQ ID NO: 25 obtained from the GenBank of the National Institute of Health (NIH GenBank), primers represented by SEQ ID NOs: 12 and 13 able to amplify the downstream region of the nadC gene, primers of SEQ ID NOs: 14 and 15 able to amplify the upstream and downstream regions of the nadC gene, and loxpCm gene, and primers of SEQ ID NOs: 16 and 17 able to amplify the upstream region of the nadC gene were constructed.

TABLE 5

| Nucleotide sequence | SEQ ID NO |
|---|---|
| 5' CATTATACGAACGGTACCCCCAGTTGAATAAACACCTCTTCA 3' | 12 |
| 5' TGGCGGCAGGCTAATATT 3' | 13 |
| 5' GTTCTTCCAGATTCTCTACTTTTCGAGCTCGGTACCTACCG 3' | 14 |

TABLE 5-continued

| Nucleotide sequence | SEQ ID NO |
|---|---|
| 5' TGAAGAGGTGTTTATTCAACTGGGGGTACCGTTCGTATAATG 3' | 15 |
| 5' ATAACCACCATCAGTTCGATA 3' | 16 |
| 5' CGGTAGGTACCGAGCTCGAAAAGTAGAGAATCTGGAAGAAC 3' | 17 |

PCR was performed using chromosomal DNA of E. coli K12 W3110 as a template and oligonucleotides of SEQ ID NOs: 12 and 13, and 16 and 17 as primers to amplify the upstream and downstream regions of nadC gene of 0.5 kb and 0.3 kb, respectively. In addition, PCR was performed using a plasmid vector including loxpCm, pLoxpCat2 vector, as a template and oligonucleotides of SEQ ID NOS. 14 and 15 as primers to amplify loxpCm gene having the sequence homologous to nadC gene on both ends of 1.0 kb. The polymerase used was PfuUltra™ DNA polymerase (Stratagene, U.S.A), and PCR was conducted by repeating 30 times of a cycle comprising denaturation at 96☐ for 30 seconds, annealing at 53☐ for 30 seconds, and extension at 72☐ for 1 minute, As a result, a nadC-upstream fragment, a nadC-downstream fragment, and a loxpCm fragment were obtained. PCR was conducted using these fragments resulting from the above-described PCR as templates under the PCR conditions including 10 repetition of the cycle comprising denaturation at 96☐ for 60 seconds, denaturation at 50☐ for 60 seconds, and extension at 72☐ for 1 minute, and 20 repetition of the cycle after addition of primers of SEQ ID NOs: 12 and 17. As a result, a nadC-deficient cassette containing the upstream region of nadC gene-/oxpCm-downstream region of nadC gene of 1.8 kb was obtained.

E. coli K12 W3110 strain containing pKD46 as expression vector of lambda red recombinase was transformed with the nadC-deficient cassette by electroporation, and then the strain was smeared on a LB plate medium (tryptone 10 g, yeast extract 5 g, NaCl 10 g, and agar 1.5%) containing chloramphenicol as a selective marker, and cultured at 37☐ overnight to select microorganism strains exhibiting resistance against chloramphenical.

The selected strains were directly used as templates to perform PCR using primers of SEQ ID NOs: 13 and 16 under the same conditions, and the gene sizes of the wild strain and the nadC-deficient strain were identified to be 1.6 kb and 1.3 kb, respectively on 1.0% agarose gel, thereby confirming the deletion of nadC gene in E. coli K12 W3110. The construction of the nadC-deficient strain, named W3110-ΔnadC, was completed.

<2-2> Construction of Plasmid for Expression of Aspartate Oxidase and Quinolinate Synthetase Two enzymes, aspartate oxidase and quinolinate synthetase, are required to produce quinolinate. Accordingly, a plasmid able to express both nadB and nadA genes encoding the two enzymes was constructed. First, PCR was performed using chromosomal DNA of E. coli W3110 to obtain nadA gene encoding quinolinate synthetase. Based on the nucleotide sequence for the nadA gene (NCBI Registration No. "GI: 89107601") represented by SEQ ID NO: 26 obtained from the GenBank of the National Institute of Health (NIH GenBank), primers of SEQ ID NOs: 18 and 19 able to amplify the ORF region of the nadA gene including ATG and TAA regions and having the recognition sites of restriction enzymes ApaI and NotI were synthesized.

TABLE 6

| Nucleotide sequence | SEQ ID NO |
|---|---|
| 5' AATTGGGCCCATGAGCGTAATGTTTGATCCA 3' | 18 |
| 5' AATTGCGGCCGCTCGTGCCTACCGCTTCG 3' | 19 |

PCR was performed using chromosomal DNA of E. coli K12 W3110 as a template, and oligonucleotides of SEQ ID NOs: 18 and 19 as primers. The polymerase used was PfuUltra™ DNA polymerase (Stratagene, U.S.A), and the PCR was conducted by repeating 30 times of a cycle comprising denaturation at 96☐ for 30 seconds, annealing at 50☐ for 30 seconds, and extension at 72☐ for 1 minute. As a result, an amplified gene of about 1.0 kb including the nadA gene and the recognition sites of restriction enzymes ApaI and NotI was obtained.

A pCJ1 promoter was obtained through PCR using a plasmid including the pCJ1 promoter as a template, based on the disclosure in Korean laid-open Patent No. 10-2006-0068505. Primers represented by SEQ ID NOs: 20 and 21 having the recognition sites of restriction enzymes BamHI and ApaI were constructed for ligating the pCJ1 promoter with the amplified nadA gene.

TABLE 7

| Nucleotide sequence | SEQ ID NO |
|---|---|
| 5' CCGCGGATCCCACCGCGGGCTTATTCCATTAC 3' | 20 |
| 5' GATGGGCCCATCTTAATCTCCTAGATTGGGTTTC 3' | 21 |

PCR was performed using chromosomal DNA of E. coli K12 W3110 as a template, and oligonucleotides of SEQ ID NOs: 20 and 21 as primers. The polymerase used was PfuUltra™ DNA polymerase (Stratagene, U.S.A), and the PCR was conducted by repeating 30 times of a cycle comprising denaturation at 96☐ for 30 seconds, annealing at 50☐ for 30 seconds, and extension at 72☐ for 1 minute. As a result, an amplified fragment of about 0.3 kb including the pCJ1 promoter and the recognition sites of the restriction enzymes BamHI and ApaI was obtained.

The nadA gene obtained through the PCR was treated with restriction enzymes ApaI and NotI, and the amplified pCJ1 promoter fragment was treated with restriction enzymes ApaI and BamHI. The nadA gene and pCJ1 promoter fragment treated with the restriction enzymes, respectively, were cloned via ligation into the pPro-nadB vector obtained in <1-1> that was treated with the restriction enzymes NotI and BamHI. Ultimately a pPro-nadB-pCJ1-nadA recombinant vector of 5.9 kb was constructed, in which the nadB gene expression is regulated by the pPro promoter as a constitutive promoter, and the nadA gene expression is regulated by pCJ1 promoter. The constructed pPro-nadB-pCJ1-nadA had the sequence represented by SEQ ID NO: 27. In addition, through the above-described processes, a recombinant vector pPro-nadB67-pCJ1-nadA including the nadB variant and the wild nadA gene was also constructed. The constructed pPro-nadB67-pCJ1-nadA had the sequence represented by SEQ ID NO: 28.

<2-2-1> Construction of Vector in which 302$^{nd}$ Amino Acid of nadB Gene of pPro-nadB67-pCJ1-nadA is Substituted with Amino Acid Except for Lysine and Arginine To confirm the resistance against NAD-feedback regulation of nadB67 gene variant, including arginine instead of lysine as the 302$^{nd}$ amino acid starting from methionine of L-aspartate oxidase, the 302$^{nd}$ amino acid of the nadB gene was substituted with each of 18 different amino acids, except for lysine and arginine. Quick mutagenesis using the recombinant vector pPro-nadB67-pCJ1-nadA as a template was performed. The polymerase used was PfuUltra™ DNA polymerase (Stratagene, U.S.A.). PCR was conducted by repeating 18 times of a cycle comprising denaturation at 96☐ for 30 seconds, annealing at 55☐ for 30 seconds, and extension at 68☐ for 15 minutes. The resulting PCR product was treated with the restriction enzyme DpnI (NEB, U.S.A), and then transformed into E. coli DH5α strain (Invitrogen, U.S.A.) via CaCl$_2$ method. The transformed E. coli DH5a strain was smeared on a LB-Km plate medium (yeast extract 10 g/L, NaCl 5 g/L, tryptone g/L, kanamycin 25 µg/L), and cultured overnight at 37☐ to select kanamycin-resistant colonies. The resulting colonies were subjected to plasmid extraction and sequencing to identify the substitution of the 302$^{nd}$ amino acid with the 18 different amino acids. The resulting 18 nadB variants as plasmids were named as in Table 2.

TABLE 8

L-aspartate oxidase variants in which 302$^{nd}$ amino acid was substituted with another amino acid

| Name | Original 302$^{nd}$ amino acid of nadB | Substituted amino acid |
| --- | --- | --- |
| pPro-nadB67-pCJ1-nadA | Lysine | Arginine |
| pPro-nadB67(G)-pCJ1-nadA | | Glycine |
| pPro-nadB67(A)-pCJ1-nadA | | Alanine |
| pPro-nadB67(S)-pCJ1-nadA | | Serine |
| pPro-nadB67(T)-pCJ1-nadA | | Threonine |
| pPro-nadB67(C)-pCJ1-nadA | | Cysteine |
| pPro-nadB67(V)-pCJ1-nadA | | Valine |
| pPro-nadB67(L)-pCJ1-nadA | | Leucine |
| pPro-nadB67(I)-pCJ1-nadA | | Isoleucine |
| pPro-nadB67(M)-pCJ1-nadA | | Methionine |
| pPro-nadB67(P)-pCJ1-nadA | | Proline |
| pPro-nadB67(F)-pCJ1-nadA | | Phenylalanine |
| pPro-nadB67(Y)-pCJ1-nadA | | Tyrosine |
| pPro-nadB67(W)-pCJ1-nadA | | Tryptophan |
| pPro-nadB67(D)-pCJ1-nadA | | Aspartic acid |
| pPro-nadB67(E)-pCJ1-nadA | | Glutamic acid |
| pPro-nadB67(N)-pCJ1-nadA | | Asparagine |
| pPro-nadB67(Q)-pCJ1-nadA | | Glutamine |
| pPro-nadB67(H)-pCJ1-nadA | | Histidine |

<2-3> Evaluation of Quinolinate-Producing Ability of Wild nadB and nadB67 Variants with Respect to NAD Concentration To compare the ability to produce quinolinate in the wild type nadB gene and nadB gene variants with respect to NAD concentration, a quinolinate titer assay was conducted. After the quinolinate-producing strain (W3110-ΔnadC) obtained in <2-1> of Example 2 was transformed with the plasmidpPro-nadB67-pCJq1-nadA constructed in <2-2> of Example 2, and each of the 18 types of nadB67 variants constructed in <2-2-1> of Example 2 via CaCl$_2$ method. The transformed strains were cultured overnight in a LB-Km plate medium in a 37☐ culture batch to obtain a single colony, and then the single colony was inoculated by one platinum pool into 25 ml of a culture medium for the quinolinate potency assay and cultured at 37☐ for 24 hours to 72 hours by shaking at 250 rpm. Table 9 shows the composition of the culture medium for producing quinolinate. To identify the NAD feedback resistance of the nadB67 variants, nicotinic acid (NA) was added to the culture medium at different concentrations, followed by comparison of the produced quantities of quinolinate.

TABLE 9

Composition of the culture medium for quinolinate potency assay

| Composition | Concentration (per liter) |
| --- | --- |
| Glucose | 70 g |
| Ammonium sulfate | 17 g |
| KH$_2$PO$_4$ | 1.0 g |
| MgSO$_4$•7H$_2$O | 0.5 g |
| FeSO$_4$•7H$_2$O | 5 mg |
| MnSO$_4$•8H$_2$O | 5 mg |
| ZnSO$_4$ | 5 mg |
| Calcium carbonate | 30 g |
| Yeast extract | 2 g |

The quantity of quinolinate (quinolinic acid, QA) in each of the culture solutions was analyzed by high performance liquid chromatography (HPLC). The results are shown in Table 10. Table 10 shows the ability to produce quinolinate of the nadB67 variants with respect to NAD concentration.

TABLE 10

Production quantities of quinolinate with respect to NAD concentrations

| | | QA (mg/L) | | |
| --- | --- | --- | --- | --- |
| Strain | Plasmid | NA 0 uM | NA 5 uM | NA 10 uM |
| W3110-ΔnadC | pPro-nadB-pCJ-nadA | 3500 | 1600 | 700 |
| | pPro-nadB67-pCJ-nadA | 4553 | 3860 | 3251 |
| | pPro-nadB67(G)-pCJ-nadA | 4560 | 3830 | 3058 |
| | pPro-nadB67(A)-pCJ-nadA | 4560 | 3830 | 3058 |
| | pPro-nadB67(S)-pCJ-nadA | 4560 | 3830 | 3058 |
| | pPro-nadB67(T)-pCJ-nadA | 4560 | 3830 | 3058 |
| | pPro-nadB67(C)-pCJ-nadA | 4560 | 3830 | 3058 |
| | pPro-nadB67(V)-pCJ-nadA | 4425 | 3937 | 3280 |
| | pPro-nadB67(L)-pCJ-nadA | 4425 | 3937 | 3280 |
| | pPro-nadB67(I)-pCJ-nadA | 4425 | 3937 | 3280 |
| | pPro-nadB67(M)-pCJ-nadA | 4425 | 3937 | 3280 |
| | pPro-nadB67(P)-pCJ-nadA | 2223 | 1879 | 1975 |
| | pPro-nadB67(F)-pCJ-nadA | 4241 | 3795 | 3141 |
| | pPro-nadB67(Y)-pCJ-nadA | 4241 | 3795 | 3141 |
| | pPro-nadB67(W)-pCJ-nadA | 4707 | 3715 | 3186 |
| | pPro-nadB67(D)-pCJ-nadA | 100 | 100 | 100 |
| | pPro-nadB67(E)-pCJ-nadA | 100 | 100 | 100 |
| | pPro-nadB67(N)-pCJ-nadA | 4552 | 3939 | 3171 |
| | pPro-nadB67(Q)-pCJ-nadA | 4552 | 3939 | 3171 |
| | pPro-nadB67(H)-pCJ-nadA | 4891 | 3751 | 3255 |

TABLE 11

Relative yield of quinolinate with respect to NAD concentration

| | | Relative Percentage (%) | | |
| --- | --- | --- | --- | --- |
| Strain | Plasmid | NA 0 uM | NA 5 uM | NA 10 uM |
| W3110-ΔnadC | pPro-nadB-pCJ-nadA | 100 | 46 | 20 |
| | pPro-nadB67-pCJ-nadA | 100 | 85 | 71 |

TABLE 11-continued

Relative yield of quinolinate with respect to NAD concentration

| | | Relative Percentage (%) | | |
|---|---|---|---|---|
| Strain | Plasmid | NA 0 uM | NA 5 uM | NA 10 uM |
| | pPro-nadB67(G)-pCJ-nadA | 100 | 84 | 67 |
| | pPro-nadB67(A)-pCJ-nadA | 100 | 84 | 67 |
| | pPro-nadB67(S)-pCJ-nadA | 100 | 84 | 67 |
| | pPro-nadB67(T)-pCJ-nadA | 100 | 84 | 67 |
| | pPro-nadB67(C)-pCJ-nadA | 100 | 84 | 67 |
| | pPro-nadB67(V)-pCJ-nadA | 100 | 89 | 74 |
| | pPro-nadB67(L)-pCJ-nadA | 100 | 89 | 74 |
| | pPro-nadB67(I)-pCJ-nadA | 100 | 89 | 74 |
| | pPro-nadB67(M)-pCJ-nadA | 100 | 89 | 74 |
| | pPro-nadB67(P)-pCJ-nadA | 100 | 85 | 89 |
| | pPro-nadB67(F)-pCJ-nadA | 100 | 89 | 74 |
| | pPro-nadB67(Y)-pCJ-nadA | 100 | 89 | 74 |
| | pPro-nadB67(W)-pCJ-nadA | 100 | 79 | 68 |
| | pPro-nadB67(D)-pCJ-nadA | 100 | 100 | 100 |
| | pPro-nadB67(E)-pCJ-nadA | 100 | 100 | 100 |
| | pPro-nadB67(N)-pCJ-nadA | 100 | 87 | 70 |
| | pPro-nadB67(Q)-pCJ-nadA | 100 | 87 | 70 |
| | pPro-nadB67(H)-pCJ-nadA | 100 | 77 | 67 |

For the two quinolinate-producing variants including the plasmids pPro-nadB67(D)-pCJ-nadA and pPro-nadB67(E)-pCJ-nadA, the nadB gene was destroyed and lost activity. As a result, the quinlinate-producing variants mostly had very low quinolinate (QA) levels, the level was converted to a residual relative yield in percentage (%). It was based on 100% of the produced QA level when a nicotinic acid (NA) is 0 uM.

Referring to Table 11, the yield of quinolinate was less than 50% when the pPro-nadB-pCJ-nadA plasmid including the wild type nadB gene was used, and the culture medium contains nicotinic acid, over 5 uM or greater. Whereas the yield of quinolinate was 70% or greater when the pPro-nadB67-pCJ-nadA plasmid and $302^{nd}$ variants recombinant plasmids including the nadB gene variant were used. W3110-ΔnadC strain is an NAD auxotroph that requires supply of external NAD for growth. W3110-ΔnadC strain is unable to directly accept NAD, and uses heterogenous nicotinic acid (NA) or nicotinamide (Nm) to produce NAD. When an amount of intracellular NAD is 1 mM or greater, the nadB gene is feedback-regulated to maintain the amount of intracellular NAD constant. Accordingly, the production of QA may be limited by the nadB gene that is feedback-regulated. Adding NA to a culture medium means an increase of NAD in a strain. Accordingly, the production quantities of QA were compared between the strains with the addition of NA to the culture medium at different concentrations to identify a degree of feedback regulation in the nadB gene variants with respect to NAD concentration. As a result, the nadB gene variants with substituted $302^{nd}$ amino acids were found that the feedback regulation by NAD is released.

<2-4> Production of Nicotinic Acid Through Decarboxylation Reaction

To identify the ability to produce nicotinic acid of the quinolinate-producing strains into which nadB variants were introduced, the yields of quinolinate in Table 10 were used. The production method of nicotinic acid used herein was decarboxylation of the quinolinate-including culture solution under high-temperature and high-pressure conditions based on the disclosure of Korean Patent No. 10-1223904, to convert quinolinate to nicotinic acid. To remove cells from the quinolinate-containing culture solution, centrifugation was performed at about 3000 rpm to about 4000 rpm for about 10 minutes to about 30 minutes. The quinolinate-containing supernatant resulting from the centrifugation was separated and used as a sample for decarboxylation reaction.

The decarboxylation reaction was conducted at about 135□ at about 0.2 MPa for about 3 hours. The samples used are shown in Table 12. An aqueous solution of quinolinate (a standard product of Sigma-Aldrich Co.) in deionized water was used as a control group. Each samples of the aqueous solutions of quinolinate was titrated with sodium hydroxide, ammonia water, hydrochloric acid, or sulfuric acid, specifically the conversion of quinolinate into nicotinic acid took place at pH of 2. Table 12 shows the production quantities of nicotinic acid converted from quinolinate of Table 10 through high-temperature and high-pressure reaction.

TABLE 12

| Strain | Plasmid | Quinolinate (mg/L) | Nicotinic acid (mg/L) |
|---|---|---|---|
| W3110-ΔnadC | pPro-nadB-pCJ-nadA | 3500 | 2555 |
| | pPro-nadB67-pCJ-nadA | 4553 | 3324 |
| | pPro-nadB67(G)-pCJ-nadA | 4560 | 3329 |
| | pPro-nadB67(A)-pCJ-nadA | 4560 | 3329 |
| | pPro-nadB67(S)-pCJ-nadA | 4560 | 3329 |
| | pPro-nadB67(T)-pCJ-nadA | 4560 | 3329 |
| | pPro-nadB67(C)-pCJ-nadA | 4560 | 3329 |
| | pPro-nadB67(V)-pCJ-nadA | 4425 | 3230 |
| | pPro-nadB67(L)-pCJ-nadA | 4425 | 3230 |
| | pPro-nadB67(I)-pCJ-nadA | 4425 | 3230 |
| | pPro-nadB67(M)-pCJ-nadA | 4425 | 3230 |
| | pPro-nadB67(P)-pCJ-nadA | 2223 | 1623 |
| | pPro-nadB67(F)-pCJ-nadA | 4241 | 3096 |
| | pPro-nadB67(Y)-pCJ-nadA | 4241 | 3096 |
| | pPro-nadB67(W)-pCJ-nadA | 4707 | 3436 |
| | pPro-nadB67(D)-pCJ-nadA | 100 | 73 |
| | pPro-nadB67(E)-pCJ-nadA | 100 | 73 |
| | pPro-nadB67(N)-pCJ-nadA | 4552 | 3323 |
| | pPro-nadB67(Q)-pCJ-nadA | 4552 | 3323 |
| | pPro-nadB67(H)-pCJ-nadA | 4891 | 3570 |

The experiment of converting quinolinate in aqueous solution (deionized water) into nicotinic acid, as disclosed in the prior reference Chinese Patent No. 101353322, was performed at 135□ and at 0.2 MPa for about 3 hours. The temperature and the pressure levels were lower than 150□ to 250 □ in the prior reference, respectively. The results are shown in Table 12.

Example 3

Confirmation of NAD Feedback Resistance Activity of L-Aspartate Oxidase Variants <3-1> Construction of L-Aspartate Oxidase Over-Expression Plasmid To more clarify the NAD-feedback resistance activities of L-aspartate oxidase variants, the NAD-feedback resistance of a L-aspartate oxidase variant encoded by the nadB67 variant selected in <Example 1-3-2> was evaluated. To clone the wild type nadB and the nadB variants into a pCDF-duet vector containing a histidine (His)-tag, PCR was performed using the wild type pPro-nadB plasmid and the recombinant pPro-nadB67 as templates, respectively. For use in PCR, primers of SEQ ID NOs: 22 and 23 able to amplify the ORF region of the wild type nadB and the variant nadB67 gene that includes ATG and TAA regions and having the recognition sites of the restriction enzymes BamHI and NdeI were constructed.

TABLE 13

| Nucleotide sequence | SEQ ID NO. |
|---|---|
| 5' AATTGGATCCGATGAATACTCTCCCTGAACATT 3' | 22 |
| 5' AATTCATATGTTATCTGTTTATGTAATGATTGC 3' | 23 |

The polymerase used was PfuUltra™ DNA polymerase (Stratagene, U.S.A), and the PCR was conducted by repeating 30 times of a cycle comprising denaturation at 96□ for 30 seconds, annealing at 50□ for 30 seconds, and extension at 72□ for 2 minutes. As a result, amplified genes of about 1.9 kb of the wild type nadB and the nadB67 variant including the recognition sites of the restriction enzymes BamHI and NdeI was obtained.

The genes of the wild type nadB and nadB67 variant obtained through the PCR was treated with the restriction enzymes BamHI and NdeI, and then cloned via ligation into a pCDF-duet vector treated with the restriction enzymes BamHI and NdeI. Ultimately recombinant vectors including the genes of the wild type nadB and the nadB67 variant, respectively, was constructed wherein the expression of each of the genes is controllable by a T7 promoter as a constitutive promoter and the gene contains the His-tag capable of protein purification. The constructed recombinant vectors were named pT7-nadB and pT7-nadB67, respectively. Other recombinant vectors in which valine, leucine, isoleucine, and histidine were substituted for the 302$^{nd}$ amino acid of the wild type nadB, respectively, were constructed using the same method, and named pT7-nadB67(V), pT7-nadB67(L), pT7-nadB67(I), pT7-nadB67(H), respectively.

<3-2> Purification of L-Aspartate Oxidase

After the recombinant vector pT7-nadB, pT7-nadB67, pT7-nadB67(V), pT7-nadB67(L), pT7-nadB67(I), or pT7-nadB67(H) was transformed into a tuner strain via CaCl$_2$ method, the transformed strain was smeared on a LB-SP (yeast extract 10 g/L, NaCl 5 g/L, tryptone 10 g/L, and spectinomycin 50 µg/L) plate medium, and cultured overnight at 37□ to select spectinomycin-resistant colonies. One colony was selected from them and cultured in a LB-SP (yeast extract 10 g/L, NaCl 5 g/L, tryptone 10 g/L, spectinomycin 50 µg/L) liquid medium, and then a isopropyl-1-thio-β-D-galactopyranoside (IPTG) derivative was added thereto when the growth optical density (OD) value reached to 0.4, and cultured at about 18□ overnight. Cells including the overexpressed wild type L-aspartate oxidase and L-aspartate oxidase variants were recovered from the culture medium, followed by purification of the wild type L-aspartate oxidase and L-aspartate oxidase variants from the recovered cells by Ni-NTA spin kit (Quiagen, U.S.A). The recovered protein was 50% of a total protein, about 2% of the recovered protein was recovered as L-aspartate oxidase.

<3-3> Activity Test of L-Aspartate Oxidase Variants

The L-aspartate oxidase converts aspartate as a substrate to iminoaspartate in the presence of an FAD as cofactor, and the imminoaspartate is converted b to oxaloacetate. Hydrogen peroxide (H$_2$O$_2$), that is generated through the above-described reaction, was used to identify the activity of the nadB. Absorbance at 560 nm of a reaction product of H$_2$O$_2$ with a product from the reaction was measured using an Amplex Red (Invitrogen, Korea) to determine the activity of the nadB. Here, NAD was added at different concentrations to create a condition for competitive inhibition to FAD so as to evaluate the resistance of L-aspartate oxidase against the feedback regulation by NAD. The Relative activity of the wild type L-aspartate oxidase at a NAD concentration of 1 mM was less than 50%, while the relative activities of the L-aspartate oxidase variants at the same NAD concentration remained about 70% or higher (Table 14), thereby indicating that the feedback regulation by NAD was released in L-aspartate oxidase variants.

TABLE 14

Activity comparison between L-aspartate oxidases with respect to NAD concentration
Relativeactivity

| NAD concentration (mM) | Relative (%) | | | | | |
|---|---|---|---|---|---|---|
| | Wild type-nadB | Variant-nadB67 | Variant-nadB67 (V) | Variant-nadB67 (L) | Variant nadB67 (I) | Variant-nadB67 (H) |
| 0 | 100 | 100 | 100 | 100 | 100 | 100 |
| 0.05 | 95 | 102 | 100 | 100 | 100 | 100 |
| 0.3 | 82 | 96 | 95 | 95 | 95 | 95 |
| 0.5 | 65 | 75 | 77 | 76 | 76 | 77 |
| 1 | 22 | 74 | 75 | 74 | 75 | 74 |

INDUSTRIAL APPLICABILITY

The present invention is related to L-aspartate oxidase variants that are resistant against the feedback regulation by nicotinic acid or NAD, and thus may effectively produce quinolinate. Quinolinate may be effectively produced by culturing of a microorganism including such a L-aspartate oxidase variant according to the embodiments of the present invention. Quinolinate may also be effectively produced using the microorganism in which the activity of quinolinate synthetase is additionally enhanced or the activity of quinolinate phosphoribosyltransferase is additionally weakened. Through such transformation of the microorganism, the yield of quinolinate or nicotinic acid may be improved, which is industrially and highly useful.

[Accession No.]
Depositary Institution: Korean Culture Center of Microorganisms (KCCM) (International Depositary Authority)
Accession No: KCCM11434
Date of deposit: Jun. 20, 2013

While the invention has been particularly shown and described with reference to exemplary embodiments thereof, it will be understood that various changes in form and details may be made therein without departing from the spirit and scope of the following claims.

The invention claimed is:

1. A polynucleotide comprising a nucleotide sequence encoding an L-aspartate oxidase variant, wherein said variant comprises an amino acid sequence having 90% or more sequence identity to SEQ ID NO: 1 and which has Lys302 substituted with another amino acid.

2. A vector comprising the polynucleotide of claim 1 which is operably linked to a regulatory sequence.

3. A microorganism comprising the polynucleotide of claim 1.

4. The microorganism according to claim 3, wherein the microorganism belongs to the genus *Escherichia*.

5. The microorganism according to claim 3, wherein the activity of quinolinate synthetase is enhanced.

6. The microorganism according to claim 3, wherein the activity of endogenous quinolinate phosphoribosyltransferase is reduced.

7. A method of producing quinolinate, the method comprising:
   culturing the microorganism of claim 3 in a medium; and
   recovering quinolinate from the cultured medium.

8. A method of producing nicotinic acid, the method comprising:
   culturing the microorganism of claim 3 in a medium; and
   conducting a decarboxylation reaction by adding an acid to the cultured medium.

9. A polynucleotide according to claim 1, wherein the another amino acid is selected from the group consisting of arginine, glycine, alanine, serine, threonine, cysteine, valine, leucine, isoleucine, methionine, proline, phenylalanine, tyrosine, tryptophan, asparagine, glutamine, and histidine.

10. A polynucleotide according to claim 1, wherein the another amino acid is selected from the group consisting of arginine, valine, leucine, isoleucine, methionine, tryptophan, and histidine.

11. A polynucleotide according to claim 1, wherein the nucleotide sequence that encoding amino acid sequence of SEQ ID NO: 1 is represented by SEQ ID NO:24.

* * * * *

SEQUENCE LISTING

<160> NUMBER OF SEQ ID NOS: 30

<210> SEQ ID NO 1
<211> LENGTH: 540
<212> TYPE: PRT
<213> ORGANISM: Artificial Sequence

```
<220> FEATURE:
<223> OTHER INFORMATION: amino acid sequence of nadB

<400> SEQUENCE: 1

Met Asn Thr Leu Pro Glu His Ser Cys Asp Val Leu Ile Ile Gly Ser
1               5                   10                  15

Gly Ala Ala Gly Leu Ser Leu Ala Leu Arg Leu Ala Asp Gln His Gln
            20                  25                  30

Val Ile Val Leu Ser Lys Gly Pro Val Thr Glu Gly Ser Thr Phe Tyr
        35                  40                  45

Ala Gln Gly Gly Ile Ala Ala Val Phe Asp Glu Thr Asp Ser Ile Asp
    50                  55                  60

Ser His Val Glu Asp Thr Leu Ile Ala Gly Ala Gly Ile Cys Asp Arg
65                  70                  75                  80

His Ala Val Glu Phe Val Ala Ser Asn Ala Arg Ser Cys Val Gln Trp
                85                  90                  95

Leu Ile Asp Gln Gly Val Leu Phe Asp Thr His Ile Gln Pro Asn Gly
            100                 105                 110

Glu Glu Ser Tyr His Leu Thr Arg Glu Gly Gly His Ser His Arg Arg
        115                 120                 125

Ile Leu His Ala Ala Asp Ala Thr Gly Arg Glu Val Glu Thr Thr Leu
    130                 135                 140

Val Ser Lys Ala Leu Asn His Pro Asn Ile Arg Val Leu Glu Arg Ser
145                 150                 155                 160

Asn Ala Val Asp Leu Ile Val Ser Asp Lys Ile Gly Leu Pro Gly Thr
                165                 170                 175

Arg Arg Val Val Gly Ala Trp Val Trp Asn Arg Asn Lys Glu Thr Val
            180                 185                 190

Glu Thr Cys His Ala Lys Ala Val Val Leu Ala Thr Gly Gly Ala Ser
        195                 200                 205

Lys Val Tyr Gln Tyr Thr Thr Asn Pro Asp Ile Ser Ser Gly Asp Gly
    210                 215                 220

Ile Ala Met Ala Trp Arg Ala Gly Cys Arg Val Ala Asn Leu Glu Phe
225                 230                 235                 240

Asn Gln Phe His Pro Thr Ala Leu Tyr His Pro Gln Ala Arg Asn Phe
                245                 250                 255

Leu Leu Thr Glu Ala Leu Arg Gly Glu Gly Ala Tyr Leu Lys Arg Pro
            260                 265                 270

Asp Gly Thr Arg Phe Met Pro Asp Phe Asp Glu Arg Gly Glu Leu Ala
        275                 280                 285

Pro Arg Asp Ile Val Ala Arg Ala Ile Asp His Glu Met Lys Arg Leu
    290                 295                 300

Gly Ala Asp Cys Met Phe Leu Asp Ile Ser His Lys Pro Ala Asp Phe
305                 310                 315                 320

Ile Arg Gln His Phe Pro Met Ile Tyr Glu Lys Leu Leu Gly Leu Gly
                325                 330                 335

Ile Asp Leu Thr Gln Glu Pro Val Pro Ile Val Pro Ala Ala His Tyr
            340                 345                 350

Thr Cys Gly Gly Val Met Val Asp Asp His Gly Arg Thr Asp Val Glu
        355                 360                 365

Gly Leu Tyr Ala Ile Gly Glu Val Ser Tyr Thr Gly Leu His Gly Ala
    370                 375                 380

Asn Arg Met Ala Ser Asn Ser Leu Leu Glu Cys Leu Val Tyr Gly Trp
385                 390                 395                 400
```

```
Ser Ala Ala Glu Asp Ile Thr Arg Arg Met Pro Tyr Ala His Asp Ile
            405                 410                 415

Ser Thr Leu Pro Pro Trp Asp Glu Ser Arg Val Glu Asn Pro Asp Glu
        420                 425                 430

Arg Val Val Ile Gln His Asn Trp His Glu Leu Arg Leu Phe Met Trp
        435                 440                 445

Asp Tyr Val Gly Ile Val Arg Thr Thr Lys Arg Leu Glu Arg Ala Leu
        450                 455                 460

Arg Arg Ile Thr Met Leu Gln Gln Glu Ile Asp Glu Tyr Tyr Ala His
465                 470                 475                 480

Phe Arg Val Ser Asn Asn Leu Leu Glu Leu Arg Asn Leu Val Gln Val
            485                 490                 495

Ala Glu Leu Ile Val Arg Cys Ala Met Met Arg Lys Glu Ser Arg Gly
            500                 505                 510

Leu His Phe Thr Leu Asp Tyr Pro Glu Leu Leu Thr His Ser Gly Pro
            515                 520                 525

Ser Ile Leu Ser Pro Gly Asn His Tyr Ile Asn Arg
            530                 535                 540

<210> SEQ ID NO 2
<211> LENGTH: 29
<212> TYPE: DNA
<213> ORGANISM: Artificial Sequence
<220> FEATURE:
<223> OTHER INFORMATION: primer for nadB

<400> SEQUENCE: 2
aattcatatg aatactctcc ctgaacatt                                29

<210> SEQ ID NO 3
<211> LENGTH: 32
<212> TYPE: DNA
<213> ORGANISM: Artificial Sequence
<220> FEATURE:
<223> OTHER INFORMATION: primer for nadB

<400> SEQUENCE: 3
aattggatcc ctataccact acgcttgatc ac                            32

<210> SEQ ID NO 4
<211> LENGTH: 22
<212> TYPE: DNA
<213> ORGANISM: Artificial Sequence
<220> FEATURE:
<223> OTHER INFORMATION: primer for nadB

<400> SEQUENCE: 4
ctcgagcata gcatttttat cc                                       22

<210> SEQ ID NO 5
<211> LENGTH: 18
<212> TYPE: DNA
<213> ORGANISM: Artificial Sequence
<220> FEATURE:
<223> OTHER INFORMATION: primer for nadB

<400> SEQUENCE: 5
cagtgagcga ggaagcgg                                            18

<210> SEQ ID NO 6
<211> LENGTH: 40
```

-continued

<210> SEQ ID NO 6
<212> TYPE: DNA
<213> ORGANISM: Artificial Sequence
<220> FEATURE:
<223> OTHER INFORMATION: primer for nadB's downstream

<400> SEQUENCE: 6
cattatacga acggtaccccc aaagcctggg tcagcgccgt                    40

<210> SEQ ID NO 7
<211> LENGTH: 19
<212> TYPE: DNA
<213> ORGANISM: Artificial Sequence
<220> FEATURE:
<223> OTHER INFORMATION: primer for nadB's downstream

<400> SEQUENCE: 7
ggcggatatt cagcagtgg                                            19

<210> SEQ ID NO 8
<211> LENGTH: 19
<212> TYPE: DNA
<213> ORGANISM: Artificial Sequence
<220> FEATURE:
<223> OTHER INFORMATION: primer for nadB's upstream

<400> SEQUENCE: 8
cccaaaccaa atttccacg                                            19

<210> SEQ ID NO 9
<211> LENGTH: 40
<212> TYPE: DNA
<213> ORGANISM: Artificial Sequence
<220> FEATURE:
<223> OTHER INFORMATION: primer for nadB's upstream

<400> SEQUENCE: 9
cggtaggtac cgagctcgaa tttctttgtt taatttacta                     40

<210> SEQ ID NO 10
<211> LENGTH: 40
<212> TYPE: DNA
<213> ORGANISM: Artificial Sequence
<220> FEATURE:
<223> OTHER INFORMATION: primer for loxpCm

<400> SEQUENCE: 10
tagtaaatta acaaagaaa ttcgagctcg gtacctaccg                      40

<210> SEQ ID NO 11
<211> LENGTH: 40
<212> TYPE: DNA
<213> ORGANISM: Artificial Sequence
<220> FEATURE:
<223> OTHER INFORMATION: primer for loxpCm

<400> SEQUENCE: 11
acggcgctga cccaggcttt ggggtaccgt tcgtataatg                     40

<210> SEQ ID NO 12
<211> LENGTH: 42
<212> TYPE: DNA
<213> ORGANISM: Artificial Sequence
<220> FEATURE:
<223> OTHER INFORMATION: primer for nadC's downstream

<400> SEQUENCE: 12

```
cattatacga acggtacccc cagttgaata aacacctctt ca                              42

<210> SEQ ID NO 13
<211> LENGTH: 18
<212> TYPE: DNA
<213> ORGANISM: Artificial Sequence
<220> FEATURE:
<223> OTHER INFORMATION: primer for nadC's downstream

<400> SEQUENCE: 13
tggcggcagg ctaatatt                                                        18

<210> SEQ ID NO 14
<211> LENGTH: 41
<212> TYPE: DNA
<213> ORGANISM: Artificial Sequence
<220> FEATURE:
<223> OTHER INFORMATION: primer for nadC's upstream

<400> SEQUENCE: 14
gttcttccag attctctact tttcgagctc ggtacctacc g                              41

<210> SEQ ID NO 15
<211> LENGTH: 42
<212> TYPE: DNA
<213> ORGANISM: Artificial Sequence
<220> FEATURE:
<223> OTHER INFORMATION: primer for nadC's upstream

<400> SEQUENCE: 15
tgaagaggtg tttattcaac tgggggtacc gttcgtataa tg                             42

<210> SEQ ID NO 16
<211> LENGTH: 21
<212> TYPE: DNA
<213> ORGANISM: Artificial Sequence
<220> FEATURE:
<223> OTHER INFORMATION: primer for loxpCm

<400> SEQUENCE: 16
ataaccacca tcagttcgat a                                                    21

<210> SEQ ID NO 17
<211> LENGTH: 41
<212> TYPE: DNA
<213> ORGANISM: Artificial Sequence
<220> FEATURE:
<223> OTHER INFORMATION: primer for loxpC

<400> SEQUENCE: 17
cggtaggtac cgagctcgaa aagtagagaa tctggaagaa c                              41

<210> SEQ ID NO 18
<211> LENGTH: 31
<212> TYPE: DNA
<213> ORGANISM: Artificial Sequence
<220> FEATURE:
<223> OTHER INFORMATION: primer for nadA

<400> SEQUENCE: 18
aattgggccc atgagcgtaa tgtttgatcc a                                         31

<210> SEQ ID NO 19
<211> LENGTH: 29
<212> TYPE: DNA
<213> ORGANISM: Artificial Sequence
```

<220> FEATURE:
<223> OTHER INFORMATION: primer for nadA

<400> SEQUENCE: 19
aattgcggcc gctcgtgcct accgcttcg                               29

<210> SEQ ID NO 20
<211> LENGTH: 32
<212> TYPE: DNA
<213> ORGANISM: Artificial Sequence
<220> FEATURE:
<223> OTHER INFORMATION: primer

<400> SEQUENCE: 20
ccgcggatcc caccgcgggc ttattccatt ac                           32

<210> SEQ ID NO 21
<211> LENGTH: 34
<212> TYPE: DNA
<213> ORGANISM: Artificial Sequence
<220> FEATURE:
<223> OTHER INFORMATION: primer

<400> SEQUENCE: 21
gatgggccca tcttaatctc ctagattggg tttc                         34

<210> SEQ ID NO 22
<211> LENGTH: 33
<212> TYPE: DNA
<213> ORGANISM: Artificial Sequence
<220> FEATURE:
<223> OTHER INFORMATION: primer

<400> SEQUENCE: 22
aattggatcc gatgaatact ctccctgaac att                          33

<210> SEQ ID NO 23
<211> LENGTH: 33
<212> TYPE: DNA
<213> ORGANISM: Artificial Sequence
<220> FEATURE:
<223> OTHER INFORMATION: primer

<400> SEQUENCE: 23
aattcatatg ttatctgttt atgtaatgat tgc                          33

<210> SEQ ID NO 24
<211> LENGTH: 1623
<212> TYPE: DNA
<213> ORGANISM: Artificial Sequence
<220> FEATURE:
<223> OTHER INFORMATION: nadB gene

<400> SEQUENCE: 24
atgaatactc tccctgaaca ttcatgtgac gtgttgatta tcggtagcgg cgcagccgga    60
ctttcactgg cgctacgcct ggctgaccag catcaggtca tcgttctaag taaaggcccg   120
gtaacggaag gttcaacatt ttatgcccag ggcggtattg ccgccgtgtt tgatgaaact   180
gacagcattg actcgcatgt ggaagacaca ttgattgccg gggctggtat ttgcgatcgc   240
catgcagttg aatttgtcgc cagcaatgca cgatcctgtg tgcaatggct aatcgaccag   300
ggggtgttgt ttgataccca cattcaaccg aatggcgaag aaagttacca tctgacccgt   360
gaaggtggac atagtcaccg tcgtattctt catgccgccg acgccaccgg tagagaagta   420

```
gaaaccacgc tggtgagcaa ggcgctgaac catccgaata ttcgcgtgct ggagcgcagc    480
aacgcggttg atctgattgt ttctgacaaa attggcctgc cgggcacgcg acgggttgtt    540
ggcgcgtggg tatggaaccg taataaagaa acggtggaaa cctgccacgc aaaagcggtg    600
gtgctggcaa ccggcggtgc gtcgaaggtt atcagtaca ccaccaatcc ggatatttct     660
tctggcgatg gcattgctat ggcgtggcgc gcaggctgcc gggttgccaa tctcgaattt    720
aatcagttcc accctaccgc gctatatcac ccacaggcac gcaatttcct gttaacagaa    780
gcactgcgcg gcgaaggcgc ttatctcaag cgcccggatg gtacgcgttt tatgcccgat    840
tttgatgagc gcggcgaact ggccccgcgc gatattgtcg cccgcgccat tgaccatgaa    900
atgaaacgcc tcggcgcaga ttgtatgttc cttgatatca gccataagcc cgccgatttt    960
attcgccagc atttcccgat gatttatgaa aagctgctcg gctggggat tgatctcaca    1020 caagaaccgg taccgattgt gcctgctgca cattatacct gcggtggtgt aatggttgat    1080
gatcatgggc gtacggacgt cgagggcttg tatgccattg gcgaggtgag ttataccggc    1140
ttacacggcg ctaaccgcat ggcctcgaat tcattgctgg agtgtctggt ctatggctgg    1200
tcggcggcgg aagatatcac cagacgtatg ccttatgccc acgacatcag tacgttaccg    1260 ccgtggggatg aaagccgcgt tgagaaccct gacgaacggg tagtaattca gcataactgg    1320
cacgagctac gtctgtttat gtgggattac gttggcattg tgcgcacaac gaagcgcctg    1380
gaacgcgccc tgcggcggat aaccatgctc aacaagaaa tagacgaata ttacgcccat    1440
ttccgcgtct caaataattt gctggagctg cgtaatctgg tacaggttgc cgagttgatt    1500
gttcgctgtg caatgatgcg taaagagagt cgggggttgc atttcacgct ggattatccg    1560
gaactgctca cccattccgg tccgtcgatc cttttcccccg gcaatcatta cataaacaga    1620
taa                                                                  1623

<210> SEQ ID NO 25
<211> LENGTH: 894
<212> TYPE: DNA
<213> ORGANISM: Artificial Sequence
<220> FEATURE:
<223> OTHER INFORMATION: nadC gene

<400> SEQUENCE: 25
atgccgcctc gccgctataa ccctgacacc cgacgtgacg agctgctgga acgcattaat     60
ctcgatatcc ccggcgcggt ggcccaggcg ctgcgggaag atttaggcgg aacagtcgat    120
gccaacaatg atattacggc aaaactttta ccggaaaatt ctcgctctca tgccacggtg    180
atcacccgcg agaatggcgt cttttgcggc aaacgctggg ttgaagaggt gtttattcaa    240
ctggcaggcg acgatgtcac cataatctgg catgtggatg acggcgatgt catcaatgcc    300
aatcaatcct tgttcgaact tgaaggccca tcccgcgtgc tgttaacggg cgaacgcact    360
gcgcttaatt ttgtgcaaac cctttcagga gttgccagta aggtacgcca ctatgtcgaa    420
ttgctggaag gcaccaacac gcagttgttg gatacgcgca aaaccttacc cggcctgcgt    480
tcagctctga atacgcggt actttgcggc ggcggagcga atcaccgtct ggggctttct    540
gatgccttcc tgatcaaaga aaaccatatt attgcctccg gctcagtgcg ccaggcggtc    600
gaaaaagcgt cctggctgca cccggatgcg ccagtagaag tcgaagtaga gaatctggaa    660
gaacttgatg aagcccctgaa agcaggagcc gatatcatca tgctggataa cttcgaaaca    720
gaacagatgc gcgaagccgt caaacgcacc aacggcaagg cgctactgga agtgtctggc    780
aacgtcactg acaaaacact gcgtgaattt gccgaaacgg gcgtggactt atctccgtc    840
```

```
ggtgcgctaa ctaaacacgt acaagcactc gacctttcaa tgcgttttcg ctaa         894
```

<210> SEQ ID NO 26
<211> LENGTH: 1044
<212> TYPE: DNA
<213> ORGANISM: Artificial Sequence
<220> FEATURE:
<223> OTHER INFORMATION: nadA gene

<400> SEQUENCE: 26

```
atgagcgtaa tgtttgatcc agacacggcg atttatcctt tcccccgaa gccgacgccg    60
ttaagcattg atgaaaaagc gtattaccgc gagaagataa aacgtctgct aaaagaacgt   120
aatgcggtga tggttgccca ctactatacc gatcccgaaa ttcaacaact ggcagaagaa   180
accggtggct gtatttctga ttctctggaa atggcgcgct tcggtgcaaa gcatcccgct   240
tctactttgt tagtcgctgg ggtgagattt atgggagaaa ccgccaaaat tctcagtccg   300
gaaaaaacaa ttctgatgcc gacacttcag gctgaatgtt cactggatct cggctgccct   360
gttgaagaat taacgcatt tgcgatgcc catcccgatc gtactgtcgt cgtctacgcc    420
aacacttctg ctgcggtaaa agcgcgcgca gattgggtgg taacttcaag cattgccgtc   480
gaacttattg atcatcttga tagtttgggt gaaaaaatca tctgggcacc cgacaaacat   540
ctggggcgtt acgtgcaaaa acagacgggt ggagacattc tatgctggca gggtgcctgt   600
attgtgcatg atgaatttaa gactcaggcg ttaacccgct tgcaagaaga atacccggat   660
gctgccatac tggtgcatcc agaatcacca caagctattg tcgatatggc ggatgcggtc   720
ggttccacca gtcaactgat cgctgctgcg aaaacattgc cacatcagag gcttattgtg   780
gcaaccgatc ggggtatttt ctacaaaatg cagcaggcgg tgccagataa agagttactg   840
gaagcaccaa ccgcaggtga gggtgcaacc tgccgcagct gcgcgcattg tccgtggatg   900
gccatgaatg gccttcaggc catcgcagag gcattagaac aggaaggaag caatcacgag   960
gttcatgttg atgaaaggct gcgagagagg gcgctggtgc cgctcaatcg tatgctggat  1020
tttgcggcta cactacgtgg ataa                                         1044
```

<210> SEQ ID NO 27
<211> LENGTH: 1
<212> TYPE: DNA
<213> ORGANISM: Artificial Sequence
<220> FEATURE:
<223> OTHER INFORMATION: pPro nadBpCJnadA

<400> SEQUENCE: 27

```
a                                                                    1
```

<210> SEQ ID NO 28
<211> LENGTH: 1
<212> TYPE: DNA
<213> ORGANISM: Artificial Sequence
<220> FEATURE:
<223> OTHER INFORMATION: pPro nadB67pCJnadA

<400> SEQUENCE: 28

```
a                                                                    1
```

<210> SEQ ID NO 29
<211> LENGTH: 347
<212> TYPE: PRT
<213> ORGANISM: Artificial Sequence
<220> FEATURE:

<223> OTHER INFORMATION: nadA-quinolinate synthase

<400> SEQUENCE: 29

```
Met Ser Val Met Phe Asp Pro Asp Thr Ala Ile Tyr Pro Phe Pro Pro
  1               5                  10                  15

Lys Pro Thr Pro Leu Ser Ile Asp Glu Lys Ala Tyr Tyr Arg Glu Lys
             20                  25                  30

Ile Lys Arg Leu Leu Lys Glu Arg Asn Ala Val Met Val Ala His Tyr
         35                  40                  45

Tyr Thr Asp Pro Glu Ile Gln Gln Leu Ala Glu Glu Thr Gly Gly Cys
     50                  55                  60

Ile Ser Asp Ser Leu Glu Met Ala Arg Phe Gly Ala Lys His Pro Ala
 65                  70                  75                  80

Ser Thr Leu Leu Val Ala Gly Val Arg Phe Met Gly Glu Thr Ala Lys
                 85                  90                  95

Ile Leu Ser Pro Glu Lys Thr Ile Leu Met Pro Thr Leu Gln Ala Glu
            100                 105                 110

Cys Ser Leu Asp Leu Gly Cys Pro Val Glu Glu Phe Asn Ala Phe Cys
        115                 120                 125

Asp Ala His Pro Asp Arg Thr Val Val Val Tyr Ala Asn Thr Ser Ala
    130                 135                 140

Ala Val Lys Ala Arg Ala Asp Trp Val Val Thr Ser Ser Ile Ala Val
145                 150                 155                 160

Glu Leu Ile Asp His Leu Asp Ser Leu Gly Glu Lys Ile Ile Trp Ala
                165                 170                 175

Pro Asp Lys His Leu Gly Arg Tyr Val Gln Lys Gln Thr Gly Gly Asp
            180                 185                 190

Ile Leu Cys Trp Gln Gly Ala Cys Ile Val His Asp Glu Phe Lys Thr
        195                 200                 205

Gln Ala Leu Thr Arg Leu Gln Glu Glu Tyr Pro Asp Ala Ala Ile Leu
    210                 215                 220

Val His Pro Glu Ser Pro Gln Ala Ile Val Asp Met Ala Asp Ala Val
225                 230                 235                 240

Gly Ser Thr Ser Gln Leu Ile Ala Ala Lys Thr Leu Pro His Gln
                245                 250                 255

Arg Leu Ile Val Ala Thr Asp Arg Gly Ile Phe Tyr Lys Met Gln Gln
            260                 265                 270

Ala Val Pro Asp Lys Glu Leu Leu Glu Ala Pro Thr Ala Gly Glu Gly
        275                 280                 285

Ala Thr Cys Arg Ser Cys Ala His Cys Pro Trp Met Ala Met Asn Gly
    290                 295                 300

Leu Gln Ala Ile Ala Glu Ala Leu Glu Gln Glu Gly Ser Asn His Glu
305                 310                 315                 320

Val His Val Asp Glu Arg Leu Arg Glu Arg Ala Leu Val Pro Leu Asn
                325                 330                 335

Arg Met Leu Asp Phe Ala Ala Thr Leu Arg Gly
            340                 345
```

<210> SEQ ID NO 30
<211> LENGTH: 297
<212> TYPE: PRT
<213> ORGANISM: Artificial Sequence
<220> FEATURE:
<223> OTHER INFORMATION: NadC - quinolinate phosphoribosyltransferase

<400> SEQUENCE: 30

```
Met Pro Pro Arg Arg Tyr Asn Pro Asp Thr Arg Arg Asp Glu Leu Leu
 1               5                  10                  15

Glu Arg Ile Asn Leu Asp Ile Pro Gly Ala Val Ala Gln Ala Leu Arg
            20                  25                  30

Glu Asp Leu Gly Gly Thr Val Asp Ala Asn Asn Asp Ile Thr Ala Lys
        35                  40                  45

Leu Leu Pro Glu Asn Ser Arg Ser His Ala Thr Val Ile Thr Arg Glu
    50                  55                  60

Asn Gly Val Phe Cys Gly Lys Arg Trp Val Glu Val Phe Ile Gln
 65                  70                  75                  80

Leu Ala Gly Asp Asp Val Thr Ile Ile Trp His Val Asp Asp Gly Asp
                85                  90                  95

Val Ile Asn Ala Asn Gln Ser Leu Phe Glu Leu Glu Gly Pro Ser Arg
            100                 105                 110

Val Leu Leu Thr Gly Glu Arg Thr Ala Leu Asn Phe Val Gln Thr Leu
        115                 120                 125

Ser Gly Val Ala Ser Lys Val Arg His Tyr Val Glu Leu Leu Glu Gly
        130                 135                 140

Thr Asn Thr Gln Leu Leu Asp Thr Arg Lys Thr Leu Pro Gly Leu Arg
145                 150                 155                 160

Ser Ala Leu Lys Tyr Ala Val Leu Cys Gly Gly Ala Asn His Arg
            165                 170                 175

Leu Gly Leu Ser Asp Ala Phe Leu Ile Lys Glu Asn His Ile Ile Ala
            180                 185                 190

Ser Gly Ser Val Arg Gln Ala Val Glu Lys Ala Ser Trp Leu His Pro
        195                 200                 205

Asp Ala Pro Val Glu Val Glu Val Glu Asn Leu Glu Glu Leu Asp Glu
        210                 215                 220

Ala Leu Lys Ala Gly Ala Asp Ile Ile Met Leu Asp Asn Phe Glu Thr
225                 230                 235                 240

Glu Gln Met Arg Glu Ala Val Lys Arg Thr Asn Gly Lys Ala Leu Leu
            245                 250                 255

Glu Val Ser Gly Asn Val Thr Asp Lys Thr Leu Arg Glu Phe Ala Glu
            260                 265                 270

Thr Gly Val Asp Phe Ile Ser Val Gly Ala Leu Thr Lys His Val Gln
        275                 280                 285

Ala Leu Asp Leu Ser Met Arg Phe Arg
        290                 295
```